United States Patent
Kang et al.

(10) Patent No.: US 8,536,347 B2
(45) Date of Patent: Sep. 17, 2013

(54) PHOTOACID GENERATOR, CHEMICALLY AMPLIFIED RESIST COMPOSITION INCLUDING THE SAME, AND ASSOCIATED METHODS

(75) Inventors: Yool Kang, Yongin-si (KR); Hak-won Kim, Seoul (KR); Weoun-ju Kim, Yongin-si (KR); Seong-woon Choi, Suwon-si (KR); Hyun-woo Kim, Seongnam-si (KR); Hai-sub Na, Suwon-si (KR); Kyoung-taek Kim, Incheon (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 1282 days.

(21) Appl. No.: 12/285,047

(22) Filed: Sep. 29, 2008

(65) Prior Publication Data
US 2009/0131684 A1    May 21, 2009

(30) Foreign Application Priority Data
Sep. 28, 2007    (KR) .................. 10-2007-0098405

(51) Int. Cl.
   *C07D 339/00*    (2006.01)
   *C07D 335/00*    (2006.01)

(52) U.S. Cl.
   USPC ............................. 549/20; 549/13

(58) Field of Classification Search
   USPC .................................... 549/20, 13
   See application file for complete search history.

(56) References Cited

U.S. PATENT DOCUMENTS

| | | | |
|---|---|---|---|
| 5,876,786 A * | 3/1999 | Zyung et al. | 427/64 |
| 6,319,649 B1 | 11/2001 | Kato et al. | |
| 6,548,220 B2 | 4/2003 | Uetani et al. | |
| 6,893,794 B2 | 5/2005 | Akita et al. | |
| 2003/0114589 A1 | 6/2003 | Suetsugu et al. | |
| 2005/0202345 A1 | 9/2005 | Kawaguchi et al. | |
| 2007/0275307 A1 | 11/2007 | Hada et al. | |

FOREIGN PATENT DOCUMENTS

| | | | |
|---|---|---|---|
| CN | 1407405 A | | 4/2003 |
| CN | 1711504 A | | 12/2005 |
| GB | 2107510 | * | 4/1983 |
| JP | 08-110638 A | | 4/1996 |
| JP | 08-240907 A | | 9/1996 |
| JP | 10-123700 A | | 5/1998 |
| JP | 11-109633 A | | 4/1999 |
| JP | 11-109634 A | | 4/1999 |
| JP | 11-218922 A | | 8/1999 |
| JP | 2002-116546 | | 4/2002 |
| JP | 2004-026789 | | 1/2004 |
| JP | 2004-109959 | | 4/2004 |
| JP | 2005-196095 | | 7/2005 |

OTHER PUBLICATIONS

Sakamizu eta I, Chem. Abs. DN124:71378 (1995).*
Jol. am. Chem. Soc. (1955) vol. 77 pp. 514-520.*
Oki et al Chem. Abs. DN 110-94189 (1988) RN 118903-88-1.*
DN 117:60751, RN 142415-42-7P (1992).*
Chinese Office Action in CN 200810165695.3, dated Nov. 23, 2011 (Kang, et al.).
Japanese Office Action dated Feb. 1, 2013.

* cited by examiner

*Primary Examiner* — Noble Jarrell
*Assistant Examiner* — Raymond Covington
(74) *Attorney, Agent, or Firm* — Lee & Morse, P.C.

(57) ABSTRACT

A photoacid generator represented by Formula 1 or Formula 2:

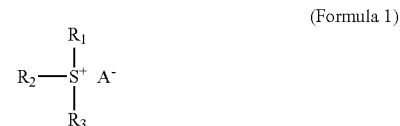

(Formula 1)

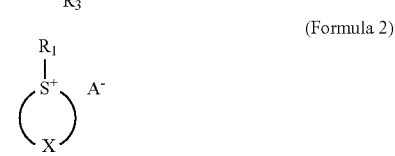

(Formula 2)

wherein $R_1$, $R_2$, and $R_3$ are each independently a C1-C10 alkyl group, X is a C3-C20 alicyclic hydrocarbon group forming a ring with $S^+$, and at least one $CH_2$ group in the alicyclic hydrocarbon group may be replaced with at least one selected from the group consisting of S, O, NH, a carbonyl group, and $R_5$—$S^+A^-$, where $R_5$ is a C1-C10 alkyl group, and $A^-$ is a counter-ion.

9 Claims, 7 Drawing Sheets

FIG. 6

TABLE 1:

| EXAMPLES | PHOTOACID GENERATORS | MOLECULAR WEIGHT | MELTING POINT (°C) | EXAMPLES | PHOTOACID GENERATORS | MOLECULAR WEIGHT | MELTING POINT (°C) |
|---|---|---|---|---|---|---|---|
| 1 | | 266.24 | 206–207 | 6 | | 240.26 | 25–30 ROOM TEMPERATURE |
| 2 | | 252.27 | 258 | 7 | | 266.30 | LIQUID |
| 3 | | 266.30 | 198–199 | 8 | | 280.33 | 42–43 |
| 4 | | 284.34 | 117–119 | 9 | | 448.44 | GEL |
| 5 | | 280.28 | 72–74 | 10 | | 268.27 | 58–60 |

PHOTOACID GENERATOR, CHEMICALLY AMPLIFIED RESIST COMPOSITION INCLUDING THE SAME, AND ASSOCIATED METHODS

BACKGROUND

1. Technical Field

Embodiments relate to a photoacid generator, a chemically amplified resist composition including the same, and associated methods.

2. Description of the Related Art

Extreme ultraviolet (EUV) lithography uses an EUV light source having a wavelength of, e.g., 13.5 nm, and is expected to replace longer-wavelength DUV lithography processes using KrF excimer lasers (248 nm) and ArF excimer lasers (193 nm). However, when the EUV lithography process is performed using a resist material including a conventional photoacid generator, acid generation efficiency and exposure rate are low, due to the low dose of acid provided by the EUV light source, thereby making it difficult to obtain a desired exposure sensitivity. Moreover, a conventional photoacid generator contains chromophore groups, which may decompose to cause a large amount of degassing in the vacuum conditions that are typical for EUV, leading to reduced process stability.

SUMMARY

Embodiments are therefore directed to a photoacid generator, a chemically amplified resist composition including the same, and associated methods, which substantially overcome one or more of the problems due to the limitations and disadvantages of the related art.

It is therefore a feature of an embodiment to provide a photoacid generator that can be manufactured using a relatively simple and inexpensive method, and has excellent photostability, allowing convenient storage and handling.

It is therefore another feature of an embodiment to provide a chemically amplified resist composition for EUV that includes a photoacid generator with a high acid generation efficiency during exposure, thereby improving the exposure sensitivity, and which is suitable for a EUV lithography process due to a relatively small degassing amount.

At least one of the above and other features and advantages may be realized by providing a photoacid generator represented by Formula 1 or Formula 2:

(Formula 1)

$$R_2—S^+—R_3 \quad A^-$$
$$\quad | \quad$$
$$\quad R_1$$

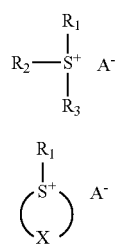

(Formula 2)

In Formula 1 and Formula 2, $R_1$, $R_2$, and $R_3$ may each independently be a C1-C10 alkyl group, C3-C20 alicyclic hydrocarbon group forming a ring with $S^+$, and at least one $CH_2$ group in the alicyclic hydrocarbon group may be replaced with at least one selected from the group consisting of S, O, NH, a carbonyl group, and $R_5$—$S^+A^-$, where $R_5$ is a C1-C10 alkyl group, and $A^-$ may be a counter-ion.

At least one $CH_2$ group of the alicyclic hydrocarbon group X may be substituted with one or more of a C1-C20 cycloalkyl group, a C1-C20 alicyclic hydrocarbon group, a C1-C20 aromatic hydrocarbon group, a hydroxyl group, a cyano group, a nitro group, or a halogen element.

The photoacid generator may be represented by Formula 1, $R_1$, $R_2$, and $R_3$ may each independently be a C1-C3 alkyl group, and $A^-$ may be a C1-C30 organic sulfonate ion substituted with F or $NH_2$.

The photoacid generator may be represented by Formula 3 or Formula 4:

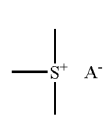

(Formula 3)

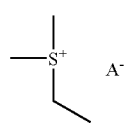

(Formula 4)

In Formula 3 and Formula 4, $A^-$ may be trifluoromethane sulfonate.

The photoacid generator may be represented by Formula 5:

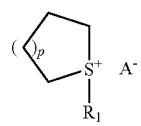

(Formula 5)

In Formula 5, p may be 1 or 2, and $A^-$ may be a C1-C30 organic sulfonate ion substituted with F or $NH_2$. $A^-$ may be trifluoromethane sulfonate.

The photoacid generator may be represented by Formula 8:

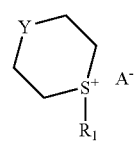

(Formula 8)

In Formula 8, Y may be S, O, NH, or a carbonyl group, and $A^-$ may be a C1-C30 organic sulfonate ion substituted with F or $NH_2$.

The photoacid generator may be represented by Formula 9, Formula 10, or Formula 11:

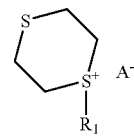

(Formula 9)

-continued

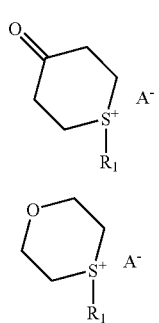
(Formula 10)

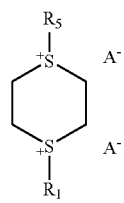
(Formula 11)

In Formulae 9-11, A⁻ may be trifluoromethane sulfonate.

The photoacid generator may be represented by Formula 12:

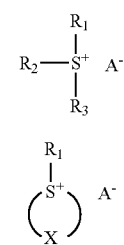
(Formula 12)

In Formula 12, A⁻ may be a C1-C30 organic sulfonate ion substituted with F or $NH_2$. A⁻ may be trifluoromethane sulfonate.

At least one of the above and other features and advantages may also be realized by providing a chemically amplified resist composition, including a polymer having a polyhydroxystyrene repeating unit, and a photoacid generator represented by Formula 1 or Formula 2:

(Formula 1)
$$R_2-\overset{R_1}{\underset{R_3}{S^+}}\ A^-$$

(Formula 2)
$$\left(\underset{X}{S^+}\right)\ A^-\ \ R_1$$

In Formula 1 and Formula 2, $R_1$, $R_2$, and $R_3$ may each independently be a C1-C10 alkyl group, X may be a C3-C20 alicyclic hydrocarbon group forming a ring with $S^+$, and at least one $CH_2$ group in the alicyclic hydrocarbon group may be replaced with at least one selected from the group consisting of S, O, NH, a carbonyl group, and $R_5$—$S^+A^-$, where $R_5$ is a C1-C10 alkyl group, and A⁻ may be a counter-ion.

The polyhydroxystyrene repeating unit may include an ethylvinyl ether protecting group or a cyclohexyl methylvinyl ether protecting group. The polymer may be a copolymer having the polyhydroxystyrene repeating unit and an acrylate repeating unit. The composition may further include a second polymer having an acrylate repeating unit mixed with the polymer having the polyhydroxystyrene repeating unit. The chemically amplified resist composition may further include an organic base.

The photoacid generator may be represented by Formula 1, $R_1$, $R_2$, and $R_3$ may each independently be a C1-C3 alkyl group, and A⁻ may be a C1-C30 organic sulfonate ion substituted with F or $NH_2$.

The photoacid generator may be represented by Formula 5:

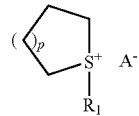
(Formula 5)

In Formula 5, p may be 1 or 2, and A⁻ may be a C1-C30 organic sulfonate ion substituted with F or $NH_2$.

The photoacid generator may be represented by Formula 8:

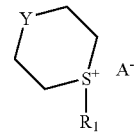
(Formula 8)

In Formula 8, Y may be S, O, NH, or a carbonyl group, and A⁻ may be a C1-C30 organic sulfonate ion substituted with F or $NH_2$.

The photoacid generator may be represented by Formula 12:

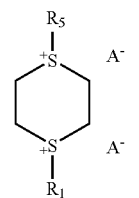
(Formula 12)

In Formula 12, $R_5$ may be a C1-C10 alkyl group, and A⁻ may be a C1-C30 organic sulfonate ion substituted with F or $NH_2$.

At least one of the above and other features and advantages may also be realized by providing a method of making a chemically amplified resist composition, the method including providing a photoacid generator, and combining the photoacid generator with a polymer having a polyhydroxystyrene repeating unit. The photoacid generator may be represented by Formula 1 or Formula 2:

(Formula 1)
$$R_2-\overset{R_1}{\underset{R_3}{S^+}}\ A^-$$

(Formula 2)
$$\left(\underset{X}{S^+}\right)\ A^-\ \ R_1$$

In Formula 1 and Formula 2, $R_1$, $R_2$, and $R_3$ may each independently be a C1-C10 alkyl group, X may be a C3-C20 alicyclic hydrocarbon group forming a ring with S⁺, and at least one CH₂ group in the alicyclic hydrocarbon group may be replaced with at least one selected from the group consisting of S, O, NH, a carbonyl group, and R₅—S⁺A⁻, where R₅ is a C1-C10 alkyl group, and A⁻ may be a counter-ion.

At least one of the above and other features and advantages may also be realized by providing a method of fabricating a device, the method including applying a chemically amplified resist composition to a substrate, exposing at least a portion of the substrate having the chemically amplified resist composition thereon to energy having a predetermined energy level, and selectively etching the substrate in a pattern produced by the exposure. The chemically amplified resist composition may include a polymer having a polyhydroxystyrene repeating unit, and a photoacid generator represented by Formula 1 or Formula 2:

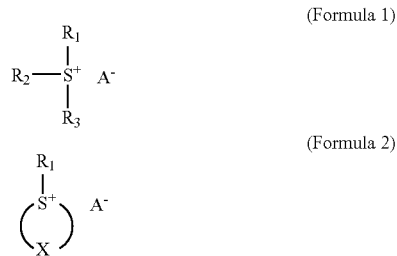

(Formula 1)

(Formula 2)

In Formula 1 and Formula 2, $R_1$, $R_2$, and $R_3$ may each independently be a C1-C10 alkyl group, X is a C3-C20 alicyclic hydrocarbon group forming a ring with S⁺, and at least one CH₂ group in the alicyclic hydrocarbon group may be replaced with at least one selected from the group consisting of S, O, NH, a carbonyl group, and R₅—S⁺A⁻, where R₅ is a C1-C10 alkyl group, and A⁻ may be a counter-ion.

The energy having a predetermined energy level may be UV light having a wavelength in the EUV region.

BRIEF DESCRIPTION OF THE DRAWINGS

The above and other features and advantages will become more apparent to those of ordinary skill in the art by describing in detail exemplary embodiments with reference to the attached drawings, in which:

FIG. 6 illustrates Table 1 setting forth data for photoacid generators obtained from Examples 1 to 10.

DETAILED DESCRIPTION OF THE EMBODIMENTS

Figure 1:
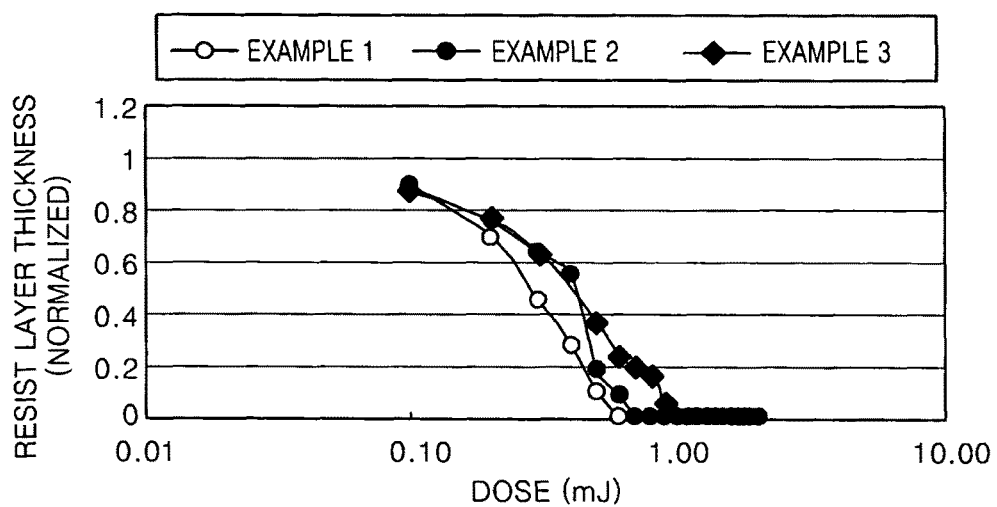
FIG. 1 illustrates a graph of a normalized contrast curve of a resist layer including a photoacid generator according to embodiments.

Korean Patent Application No. 10-2007-0098405, filed on Sep. 28, 2007, in the Korean Intellectual Property Office, and entitled: "Photoacid Generator and Chemically Amplified Resist Composition Including the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

As used herein, the expressions "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" includes the following meanings: A alone; B alone; C alone; both A and B together; both A and C together; both B and C together; and all three of A, B, and C together. Further, these expressions are open-ended, unless expressly designated to the contrary by their combination with the term "consisting of." For example, the expression "at least one of A, B, and C" may also include an $n^{th}$ member, where n is greater than 3, whereas the expression "at least one selected from the group consisting of A, B, and C" does not.

As used herein, the expression "or" is not an "exclusive or" unless it is used in conjunction with the term "either." For example, the expression "A, B, or C" includes A alone; B alone; C alone; both A and B together; both A and C together; both B and C together; and all three of A, B, and C together, whereas the expression "either A, B, or C" means one of A alone, B alone, and C alone, and does not mean any of both A and B together; both A and C together; both B and C together; and all three of A, B, and C together.

As used herein, the terms "a" and "an" are open terms that may be used in conjunction with singular items or with plural items. For example, the term "a polymer" may represent a single compound, e.g., a polyhydroxystyrene polymer, or multiple compounds in combination, e.g., a polyhydroxystyrene polymer mixed with an acrylate polymer.

As used herein, molecular weights of polymeric materials are weight average molecular weights, unless otherwise indicated.

As used herein, the terms "alkane," "alkyl group," and "alicyclic hydrocarbon group," refer to saturated hydrocarbons, whereas the terms "alkene," "cyclic alkenes," and "aryl groups" refer to a hydrocarbon having at least one carbon-carbon double bond.

A photoacid generator according to the present invention may be represented by Formulae 1 or Formula 2, below.

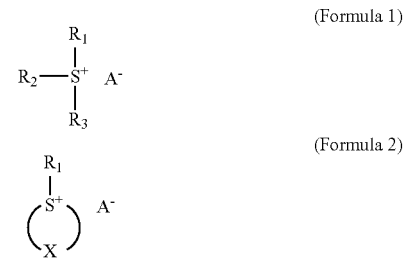

(Formula 1)

(Formula 2)

In Formulae 1 and 2, S is sulfur. In Formula 1, $R_1$, $R_2$, and $R_3$ may each be a C1-C10 alkyl group. In another embodiment, $R_1$, $R_2$, and $R_3$ may each be a C3-C6 cycloalkyl group. In Formula 2, $R_1$ may be a C5-C6 ring compound with double bonds, such as phenyl or thiophene. The cycloalkyl groups and ring compounds may include one or more of, e.g., a carbonyl group such as ketone or ester, a hydroxyl group, a cyano group, a nitro group, or a halogen element such as F, Cl, Br, or I.

In Formula 2, X may be a C3-C20 alicyclic hydrocarbon group. Preferably, X is a C4-C5 alicyclic hydrocarbon group, forming a ring with $S^+$ of Formula 2.

In an embodiment, Formula 2 may be represented by Formula 2', below.

(Formula 2')

In Formula 2', X may be a C3-C20 alicyclic hydrocarbon group forming a ring with $S^+$, and one or more $CH_2$ groups in the alicyclic hydrocarbon group may be replaced by S, O, NH, a carbonyl group, or $R_5$—$S^+A^-$, where S is in the alicyclic ring and $R_5$ is a C1-C10 alkyl group (see Formula 12, below). In Formula 2', $R_1$ may be a C5-C6 ring compound with double bonds, such as phenyl or thiophene.

In Formula 2', $R_4$ may be a C1-C20 alkyl group, a C1-C20 cycloalkyl group, a C1-C20 alicyclic hydrocarbon group, a C1-C20 aromatic hydrocarbon group, a hydroxyl group, a cyano group, a nitro group, or a halogen element.

In Formula 2', n may be 0 or 1. In Formula 1, $R_2$ and $R_3$ may form a ring with $S^+$ to have a —$R_2$—$R_3$— bond, such that Formula 1 can be represented as Formula 2 when n=0.

In Formulae 1 and 2, $A^-$ represents a counter-ion.

In an embodiment, the photoacid generator may have the structure of Formula 1 in which $R_1$, $R_2$, and $R_3$ are each independently a C1-C3 alkyl group, and $A^-$ may be, e.g., a C1-C30 organic sulfonate ion substituted with F or $NH_2$. More specifically, the photoacid generator according to the present invention may be represented by Formulae 3 or Formula 4:

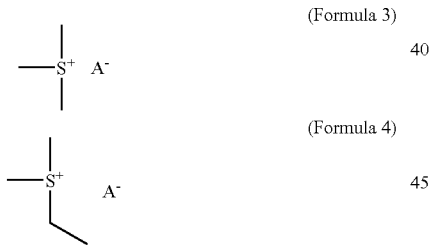

(Formula 3)

(Formula 4)

In Formula 3, three methyl groups are present, and in Formula 4, two methyl groups and an ethyl group are present. In an implementation, $A^-$ may include trifluoromethane sulfonate.

As another example, the photoacid generator according to an embodiment may be represented by Formula 5:

(Formula 5)

In Formula 5, p may be 1 or 2, and $A^-$ may include a C1-C30 organic sulfonate ion substituted with F or $NH_2$. Specific examples of the photoacid generator represented by Formula 5 may be represented by Formulae 6 and 7:

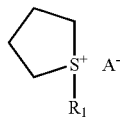

(Formula 6)

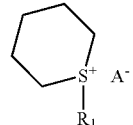

(Formula 7)

In an implementation, $A^-$ may include trifluoromethane sulfonate.

As another example, the photoacid generator according to an embodiment may be represented by Formula 8:

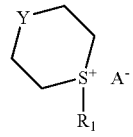

(Formula 8)

In Formula 8, Y may be an S, O, NH, or carbonyl group, and $A^-$ may include a C1-C30 organic sulfonate ion substituted with F or $NH_2$. Specific examples of the photoacid generator represented by Formula 8 may be represented by Formulae 9, 10, and 11:

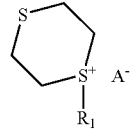

(Formula 9)

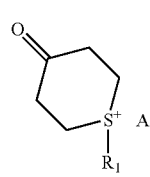

(Formula 10)

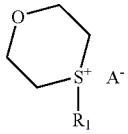

(Formula 11)

In an implementation, $A^-$ may include trifluoromethane sulfonate.

As described above in connection with Formula 2', in another example, the photoacid generator according to an embodiment may be represented by Formula 12:

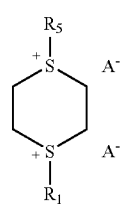

(Formula 12)

In Formula 12, A⁻ may include a C1-C30 organic sulfonate ion substituted with F or $NH_2$. In an implementation, A⁻ may include trifluoromethane sulfonate.

The photoacid generator according to embodiments may include $R_1$, $R_2$, and $R_3$ with relatively low molecular weights, and without including a chromophore group in a positive ion part. Therefore, manufacturing may be convenient, and stability against light may be excellent.

The photoacid generator according embodiments may have a high acid generating efficiency as compared to conventional photoacid generators, thus enabling a high exposure sensitivity by adding just a small amount, e.g., about 3 to about 6% by weight ("wt %") based on the total amount of the polymer included in the resist material, when used as a resist material for a EUV lithography process. Further, the photoacid generator may provide high contrast. In addition, the photoacid generator according to embodiments may be decomposed into low molecular weight materials with few negative effects due to degassing during exposure, thereby enabling a stable EUV lithography process.

A chemically amplified resist composition according to an embodiment may include a polymer having a repeating unit, the alkaline solubility of the polymer being changed by acidic action, and the photoacid generator represented by Formula 1 or 2.

In the chemically amplified resist composition according to an embodiment, the polymer may include a repeating unit that generates phenolic acid and its corresponding Brφonsted acid by acidic action. For example, the polymer may include a first repeating unit derived from polyhydroxystyrene. In addition, the first repeating unit of the polymer may have an ethylvinyl ether group or a cyclohexyl methylvinyl ether group as a protecting group.

In the chemically amplified resist composition according to an embodiment, the acid generated from the photoacid generator by exposure may act upon the protecting group of the polymer to be deprotected. As a result, the deprotected polymer may be changed to become soluble in alkaline conditions.

The polymer may have a structure where a second repeating unit derived from an acrylate forms a copolymer with the first repeating unit.

In another embodiment, the chemically amplified resist composition may be include a blend of a first polymer including a first repeating unit derived from polyhydroxystyrene, and a second polymer having a second repeating unit derived from an acrylate.

In the chemically amplified resist composition according to an embodiment, the photoacid generator may be included in an amount of about 0.1 to about 5.0 wt % based on a total weight of the polymer.

In an implementation, the chemically amplified resist composition according to an embodiment may further include an organic base. The organic base may include an organic compound containing nitrogen. For example, the organic base may include an aliphatic amine. The amount of the organic base may be about 0.01 to about 5.0 wt % based on a total weight of the polymer.

Figure 7:
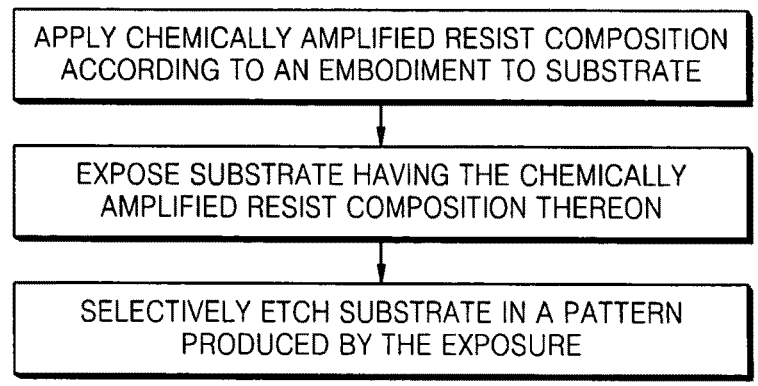
FIG. 7 illustrates an example method of fabricating a device according to an embodiment.

FIG. 7 illustrates an example method of fabricating a device according to an embodiment. Referring to FIG. 7, the chemically amplified resist composition may be employed in the fabrication of a device, e.g., a semiconductor device, an optical device, an optoelectronic device, etc. The chemically amplified resist composition may be coated on a substrate, e.g., a wafer. In an implementation, the coated wafer may be pre-baked. Subsequently, the resulting resist layer may be exposed to energy having a predetermined energy level, e.g., UV light having a wavelength of 13.5 nm. In an implementation, the resist layer may be further processed after exposure, e.g., with a post-exposure bake. The exposed resist layer may then be developed to form a pattern, e.g., using 2.38% TMAH developing solution, and rinsed using DI water. The pattern may then be used to etch the substrate according to the pattern.

The photoacid generator and the chemically amplified resist composition according to embodiments will now be described in further detail with reference to the following examples. These examples are for illustrative purposes only, are provided to aid in understanding the synthesis steps of the photoacid generator and the chemically amplified resist composition, and are not intended to limit the scope of the present invention.

EXAMPLE 1

Synthesis of a Photoacid Generator (I)

Synthesis of Trimethylsulfonium Triflate 16 mmol of dimethyl sulfide was dissolved in 10 ml of dichloromethane at 0° C., and about 17 mmol of methyltrifluoromethane sulfonate was slowly dripped to the mixture to obtain a white solid product. The solid product was filtered and dried for 1 hour in an oven at 50° C. to obtain the following product:

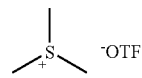

where ⁻OTf represents a negative ion of trifluoromethane sulfonate ("triflate").

Melting point ("m. p."): 206-207° C.

¹H NMR (300 MHz, $D_2O$, δ, ppm): 2.73 (s, 9H).

EXAMPLE 2

Synthesis of a Photoacid Generator (II)

Synthesis of Methyl-Tetrahydrothiophene Triflate 11 mmol of tetrahydrothiophene was dissolved in 10 ml of dichloromethane at 0° C., and about 12 mmol of methyltrifluoromethane sulfonate was slowly dripped to the mixture. As a result, a white solid product in a salt form was obtained after about 5 minutes. The solid product was filtered and dried for 1 hour in an oven at 50° C. to obtain the following product:

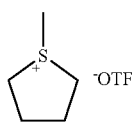

m. p.: 258° C.
$^1$H NMR (300 MHz, D$_2$O, δ, ppm): 2.11-2.23 (t, t, 4H), 2.61 (s, 3H), 3.18 (t, 2H), 3.41 (t, 2H).

EXAMPLE 3

Synthesis of a Photoacid Generator (III)
Synthesis of Methyl-Pentahydrothiopyran Triflate
5 mmol of pentahydrothiopyran was dissolved in 5 ml of dichloromethane at 0° C., and about 6 mmol of methyltrifluoromethane sulfonate was slowly dripped to the mixture. As a result, a white solid product in a salt form was obtained after about 2 minutes. The solid product was filtered and dried for 1 hour in an oven at 50° C. to obtain the following product:

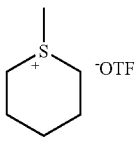

m. p.: 198-199° C.
$^1$H NMR (300 MHz, D$_2$O, δ, ppm): 1.53 (t, 2H), 1.75 (t, 2H), 1.96 (t, 2H), 2.7 (s, 3H), 2.96 (t, 2H), 3.29 (t, 2H).

EXAMPLE 4

Synthesis of a Photoacid Generator (IV)
Synthesis of Methyl-Tetrahydrothiopyran-4-One Triflate
2 mmol of tetrahydrothiopyran-4-one was dissolved in 5 ml of dichloromethane at 0° C., and about 2 mmol of methyltrifluoromethane sulfonate was slowly dripped to the mixture. The solvent was removed after about 30 minutes, and was then recrystallized with a mixture of ethyl acetate and hexane (1:2 by weight) to obtain a white solid product. The solid product was filtered and dried for 1 hour in an oven at 50° C. to obtain the following product:

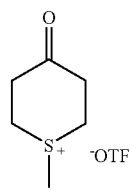

m. p.: 72-74° C.
$^1$H NMR (300 MHz, D$_2$O, δ, ppm): 2.01-2.12 (m, 4H), 2.73 (s, 3H), 3.22 (t, 2H), 3.44 (t, 2H).

EXAMPLE 5

Synthesis of a Photoacid Generator (V)
Synthesis of Methyl-Dithiane Triflate
2 mmol of 1,4-dithiane was dissolved in 8 ml of tetrahydrofuran at 0° C., and about 2 mmol of methyltrifluoromethane sulfonate was slowly dripped to the mixture. After 20 minutes a white solid product was obtained in a salt form. The solid product was filtered and dried for 1 hour in an oven at 50° C. to obtain the following product:

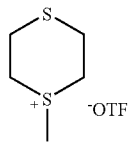

m. p.: 117-119° C.
$^1$H NMR (300 MHz, D$_2$O, δ, ppm): 2.8 (s, 3H), 2.91-2.99 (q, 2H), 3.05-3.12 (q, 2H), 3.3 (t, 2H), 3.63 (t, 2H)

EXAMPLES 6 to 10

Photoacid Generator (VI) to (X)
Photoacid generators similar to photoacid generators obtained from each of Examples 1 to 5 were synthesized with methods similar to those used in Examples 1 to 5.
Structures, molecular weights, and melting points of each of the photoacid generators obtained from Examples 1 to 5 and each of the photoacid generators according to Examples 6 to 10 are shown in Table 1 in FIG. 6.

EXAMPLE 11

Synthesis of Chemically Amplified Resist Compositions
10 g of polymer composed of PHS (polyhydroxystyrene) repeating units having EVE (ethyl vinyl ether) as a protecting group, 1.09 mmol of respective photoacid generators each synthesized from Examples 1 to 5, and 0.328 mmol of triethanolamine were each added to a solvent mixture with 157 g of PGMEA (propylene glycol monomethyl ether acetate) and 67.6 g of EL (ethyl lactate), stirred for 24 hours, and then filtered using a 0.02 μm filter to produce 5 different types of resist compositions respectively including the photoacid generators of Examples 1 to 5.

EXAMPLE 12

Figure 2:
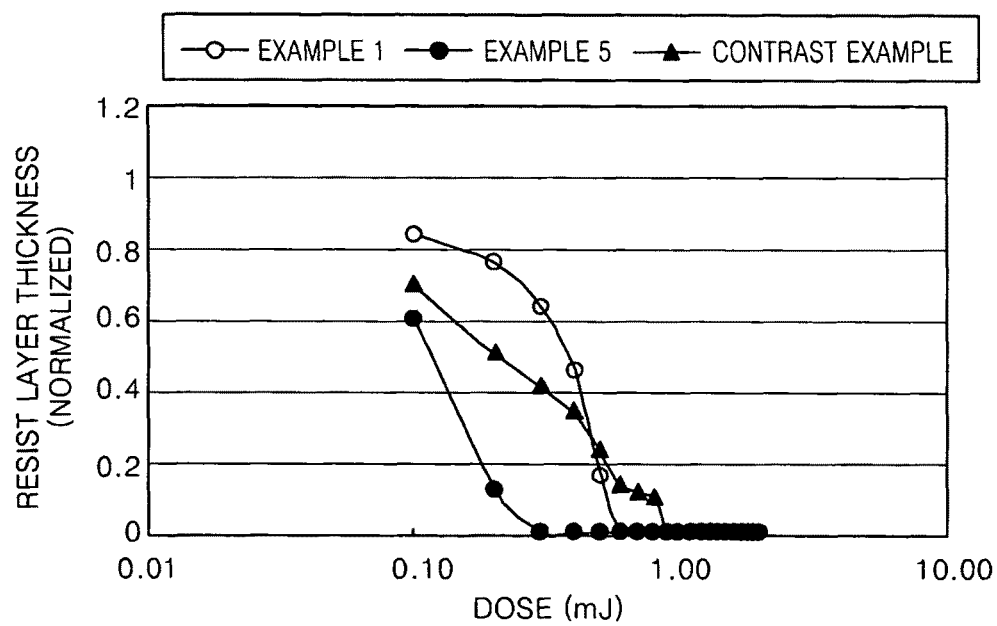
FIG. 2 illustrates a graph of a normalized contrast curve of a resist layer including a photoacid generator according to embodiments.

Evaluations of EUV Exposure and Contrast
Each resist composition produced in Example 11 was coated on a 6-inch wafer and was pre-baked for 60 seconds at 130° C. to form a resist layer with a thickness of 100 nm. Then, predetermined parts of the respective resist layers were exposed using a EUV lithography apparatus (TEUVL-2, Dong-Jin SemiChem), with a light source having a wavelength of 13.5 nm at different dose levels, increasing by 0.1 mJ within the energy range of 0 mJ to 2 mJ.
After the exposure of the resist layers, PEB (post-exposure bake) was performed for 60 seconds at 110° C., and then each wafer was cooled on a cooling plate at a temperature of 23° C. Then, the resulting products were developed for 60 seconds using 2.38% TMAH (tetramethyl ammonium hydroxide) and then rinsed with deionized ("DI") water.
The thicknesses of each of the parts exposed at different dose levels on the resist layer were measured.
FIGS. 1 and 2 are normalized contrast curves illustrating the thickness changes of the resist layers according to dose levels during exposure.
In FIG. 1, results are shown with regards to the measurements obtained on the resist layer including the photoacid generators each synthesized from Examples 1, 2, and 3.

In FIG. 2, results are shown with regards to the measurements obtained on the resist layer including the photoacid generators each synthesized from Examples 1 and 5. Moreover, FIG. 2 shows a result of evaluating the resist layer which includes triphenyl sulfonium triflate photoacid generator with a chromophore group under the same conditions as the case of the present invention as a contrast example.

From the results shown in FIGS. 1 and 2, each resist layer including the photoacid generators according to embodiments had a dose level of less than 1 mJ when the thickness became 0. In addition, the slope of the curve showing the thickness change of the resist layer is larger than the slope for the contrast example. Thus, it is apparent that the photoacid generators according to embodiments may exhibit a superior acid generating efficiency as compared to the contrast example, and may provide improved contrast characteristics and fast exposure rate.

A EUV lithography process which uses the resist layer including the photoacid generator according to embodiments may provide a good sidewall profile in a resist pattern obtained after development, due to the high acid generating efficiency and improved contrast characteristics.

EXAMPLE 13

Evaluation of Degassing Levels

Figure 3:
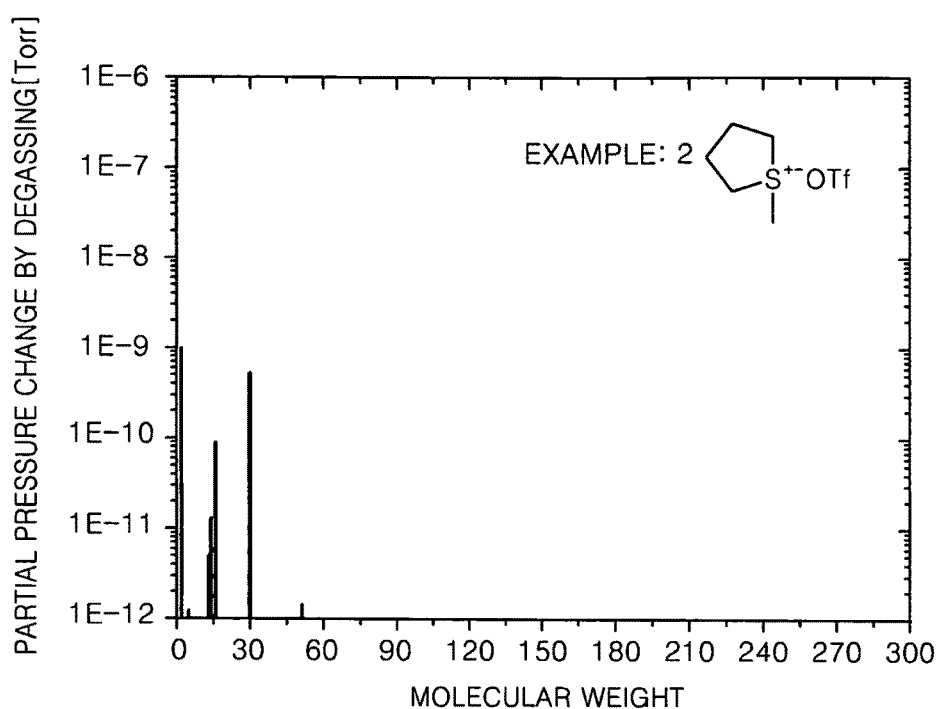
FIG. 3 illustrates a graph of partial pressure changes caused by degassing after exposure of a the resist layer according to an embodiment.

FIG. 3 is a graph illustrating the measured values of the partial pressure change caused by degassing after exposure on a resist layer including the photoacid generator according to the present invention.

Referring to FIG. 3, the resist layer formed with the resist composition produced according to Example 11 using the photoacid generator synthesized from Example 2 was exposed in an exposure area of 2.37E-1 cm$^2$, with a light source having a wavelength of 13.5 nm using EUV lithography equipment (TEUVL-2, Dong-Jin SemiChem), and the partial pressure changes with regards to the molecular weights of the components with increased partial pressure within the EUV exposure chamber were determined.

From the results shown in FIG. 3, an increase in the degassing level is apparent after the exposure, at 2.20E+12 molecules/cm$^2$. Nonetheless, considering that the acceptable limit of SAMTECH, which is a standard gauge for measuring the degassing level from resist layers caused by EUV irradiation under vacuum during EUV lithography processes, is 6.5E+13 molecules/cm$^2$, the resist composition according to embodiments may be well suited for use in EUV lithography processes. Moreover, the degassed constituents are low molecular weight components, with molecular weights of less than 60, and the quantities are very small. Therefore, EUV lithography processes performed under vacuum should not be negatively affected.

EXAMPLE 14

Evaluating Stability Against Heat

In order to evaluate the stability of the photoacid generators according to embodiments against heat, molecular weight loss of the photoacid generators was measured using a thermogravimetric analyzer (Pyris 6 TGA, Perkin Elmer) within a range of 40° C. to 500° C., increasing at a rate of 10° C./min.

Figure 4:
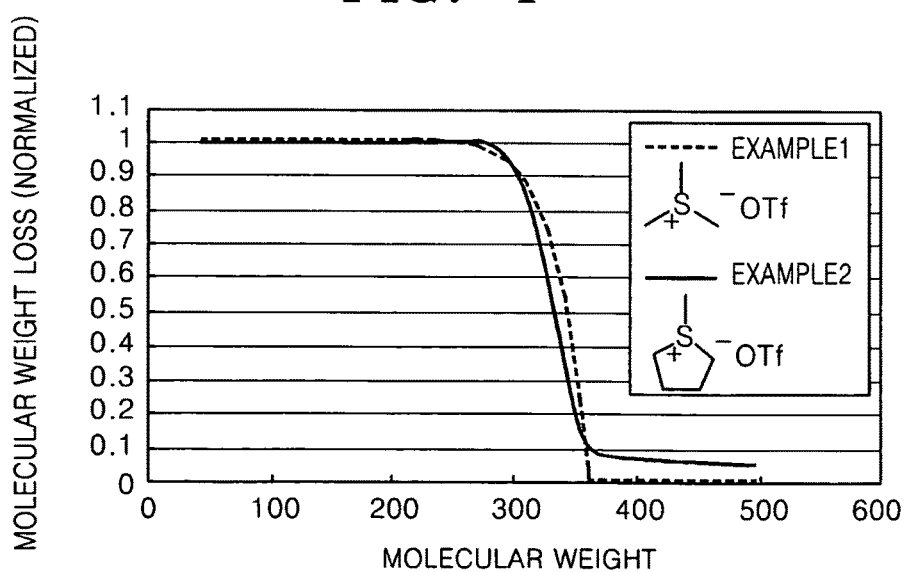
FIG. 4 illustrates a graph of a thermal analysis of a photoacid generator according to embodiments.

FIG. 4 is a graph showing the thermal analysis results evaluated using the method described above for the photoacid generators synthesized from Examples 1 and 2.

Referring to FIG. 4, each photoacid generator synthesized from Examples 1 and 2 had a decomposition temperature of about 350° C. to 360° C. From the results shown in FIG. 4, it is apparent that the photoacid generators synthesized from Examples 1 and 2 should exhibit an acceptable decomposition temperature during a lithography process.

EXAMPLE 15

Forming Resist Patterns

Each resist composition produced in Example 11 was coated on a 4-inch wafer and pre-baked at 130° C. for 60 seconds to form a resist layer 100 nm in thickness.

Subsequently, the respective resist layers were exposed to light having a wavelength of 13.5 nm using a LBNL (Lawrence Berkeley National Laboratory) MET (Micro Exposure Tool). The exposed resist layers were subjected to PEB at 110° C. for 60 seconds and then cooled on a cooling plate at a temperature of 23° C. Then, the resist layers were developed using 2.38% TMAH developing solution and rinsed using DI water.

Figure 5A:
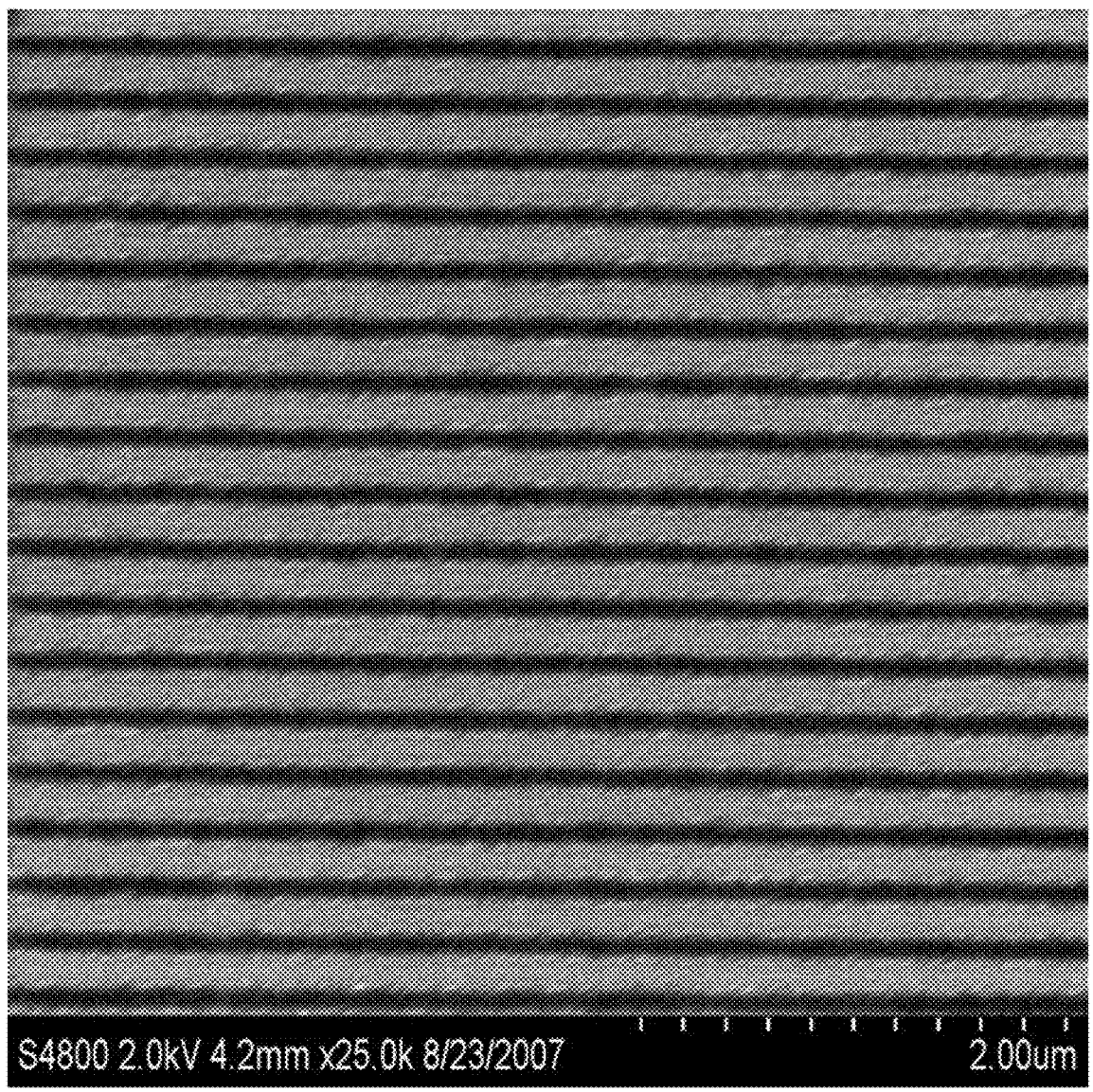
FIGS. 5A, 5B, and 5C illustrate scanning electron microscope (SEM) images of resist patterns formed using resist compositions according to embodiments.
Figure 5B:
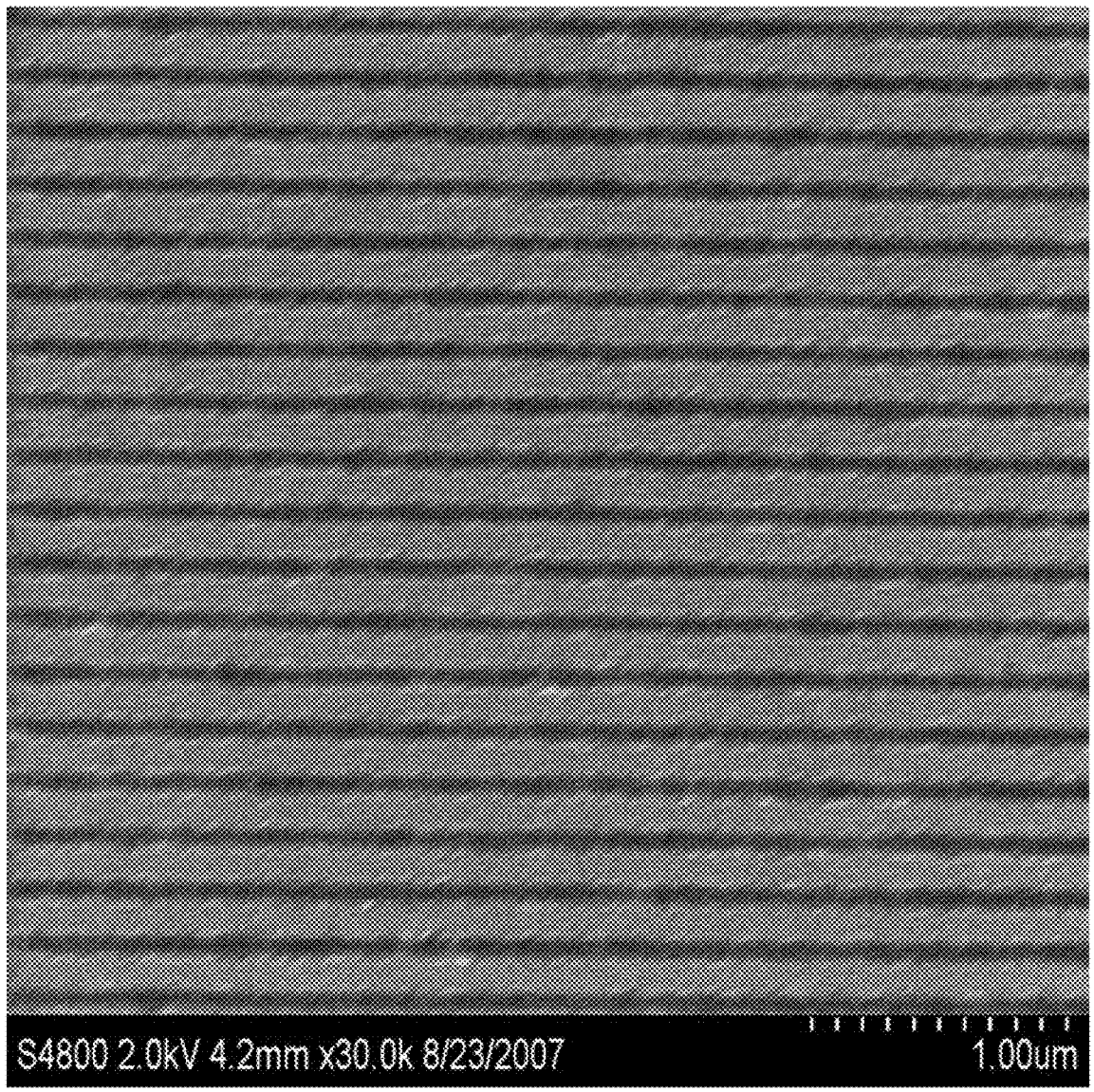
Figure 5C:
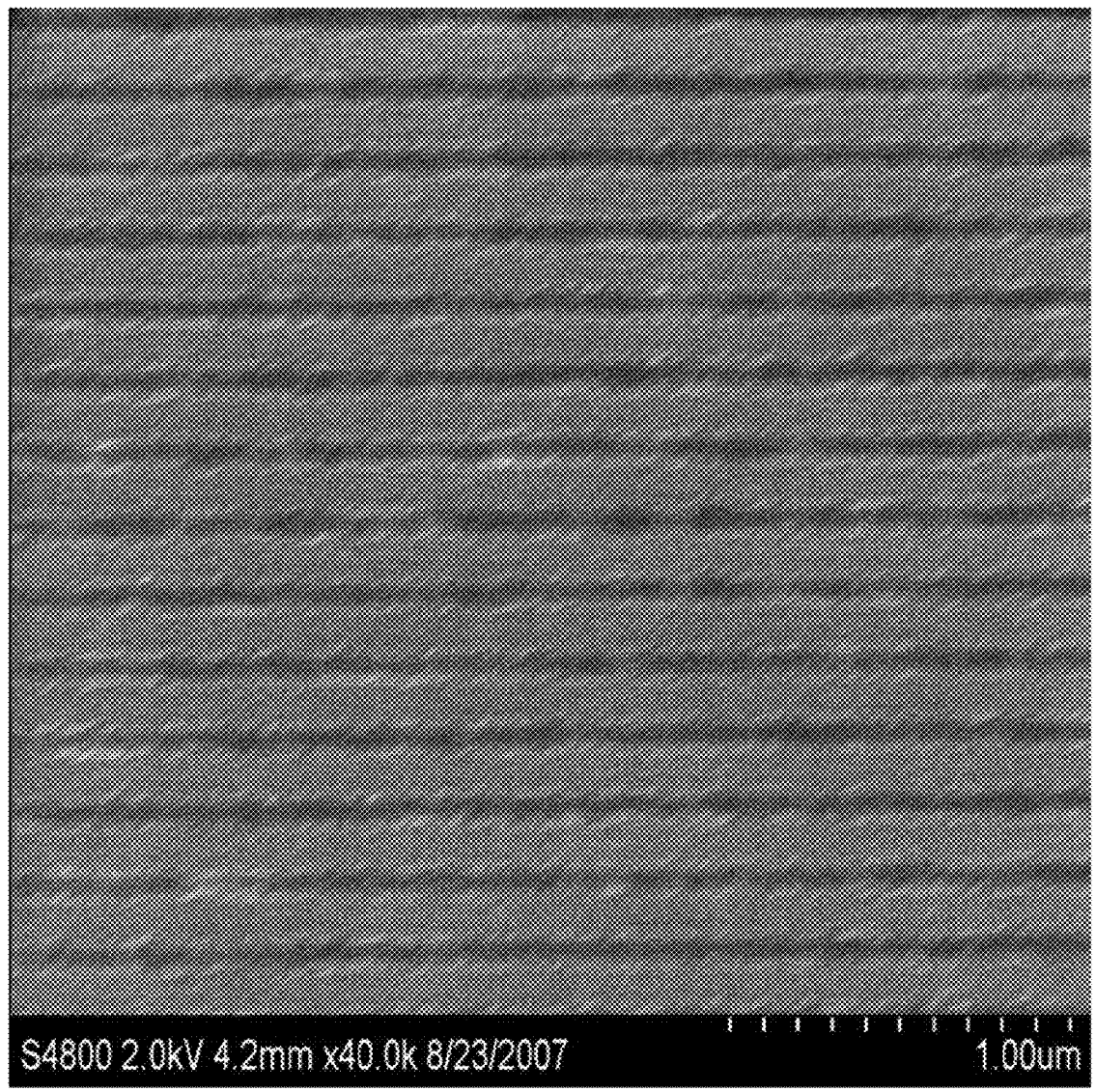

FIGS. 5A, 5B, and 5C illustrate SEM images each showing a line and space pattern formed according to the process of Example 15, with a half pitch of 100 nm, 80 nm, and 60 nm, respectively.

Referring to FIGS. 5A, 5B, and 5C, it can be seen that the photoacid generator and the resist composition according to embodiments may form a desired fine pitch pattern during EUV lithography.

The photoacid generator according to embodiments may have a low molecular weight substituent group, instead of a chromophore group which is sensitive to light, and may thus exhibit little or no negative effects caused by degassing. Accordingly, embodiments may provide convenient manufacturing and a superior stability against light, thereby allowing convenient storage and handling. In addition, the chemically amplified resist composition according to embodiments may provide superior acid generating efficiency even under a low dose, and providing an improved exposure sensitivity and contrast.

The chemically amplified composition including the photoacid generator according to embodiments may have a low manufacturing cost, allowing commercial use in EUV lithography process due to its low cost. Therefore, embodiments may be advantageous in regards to the productivity and process stability when applying EUV lithography for manufacturing highly integrated semiconductor devices, thereby allowing beneficial use in the manufacture of next-generation, highly integrated semiconductor devices.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:
1. A photoacid generator represented by Formula 2:

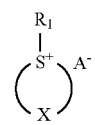

(Formula 2)

wherein:

$R_1$ is a C 1-C 10 alkyl group,

X is a C3-C20 alicyclic hydrocarbon group forming a ring with $S^+$, $CH_2$ groups in the alicyclic hydrocarbon group are unsubstituted, and at least one $CH_2$ group in the alicyclic hydrocarbon group is replaced with at least one of S, O, NH, a carbonyl group, or a $R_5$—$S^+A^-$ moiety represented by Formula 2a,

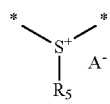

(Formula 2a)

where, in Formula 2a, * is a site where the $R_5$—$S^+A^-$ moiety is bonded in the ring, and $R_5$ is a C1-C10 alkyl group, and in Formulae 2 and 2a, $A^-$ is a C1-C30 organic sulfonate ion substituted with F or $NH_2$.

2. The photoacid generator as claimed in claim 1, wherein:

the photoacid generator is represented by Formula 8:

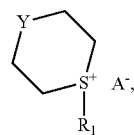

(Formula 8)

and

Y is S, O, NH, or a carbonyl group.

3. The photoacid generator as claimed in claim 2, wherein:

the photoacid generator is represented by Formula 9, Formula 10, or Formula 11:

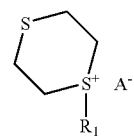

(Formula 9)

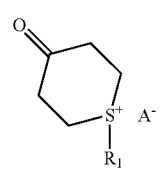

(Formula 10)

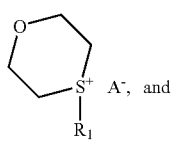

(Formula 11)

$A^-$ is trifluoromethane sulfonate.

4. The photoacid generator as claimed in claim 1, wherein:

the photoacid generator is represented by Formula 12:

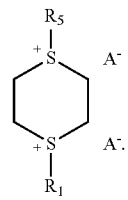

(Formula 12)

5. The photoacid generator as claimed in claim 4, wherein $A^-$ is trifluoromethane sulfonate.

6. A photoacid generator represented by Formula 2:

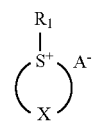

(Formula 2)

wherein:

$R_1$ is a C1-C10 alkyl group,

X is a C5-C20 alicyclic hydrocarbon group forming a ring with $S^+$, at least one $CH_2$ group in the alicyclic hydrocarbon group may be substituted, and at least one $CH_2$ group in the alicyclic hydrocarbon group is replaced with at least one of S, O, NH, a carbonyl group, or a $R_5$—$S^+A^-$ moiety represented by Formula 2a,

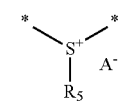

(Formula 2a)

where, in Formula 2a, * is a site where the $R_5$—$S^+A^-$ moiety is bonded in the ring, and $R_5$ is a C1-C10 alkyl group, and in Formulae 2 and 2a, $A^-$ is a C1-C30 organic sulfonate ion substituted with F or $NH_2$.

7. The photoacid generator as claimed in claim 6, wherein at least one $CH_2$ group of the alicyclic hydrocarbon group X is substituted with one or more of a C1-C20 cycloalkyl group, a C1-C20 alicyclic hydrocarbon group, a C1-C20 aromatic hydrocarbon group, a hydroxyl group, a cyano group, a nitro group, or a halogen element.

8. A photoacid generator represented by Formula 8 or Formula 12:
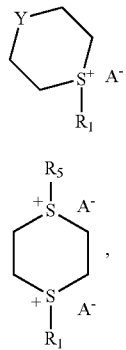
(Formula 8)
(Formula 12)
wherein:
$R_1$ is a C1-C10 alkyl group,
$R_5$ is a C1-C10 alkyl group,
Y is S, O, NH, or a carbonyl group, and
$A^-$ is trifluoromethane sulfonate.
9. The photoacid generator as claimed in claim 8, wherein the photoacid generator is represented by Formula 9, Formula 10, or Formula 11:
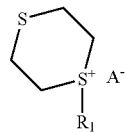
(Formula 9)
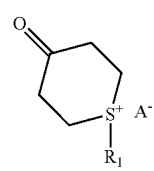
(Formula 10)
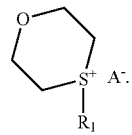
(Formula 11)
* * * * *